United States Patent
Park et al.

(10) Patent No.: US 6,991,914 B2
(45) Date of Patent: Jan. 31, 2006

(54) SILENT MARKER FOR AN OIL PRODUCT AND ASSOCIATED DETECTION METHOD

(75) Inventors: Hwan-Ho Park, Taejon (KR); Dong-Hyon Sheen, Taejon (KR); Hyun-Seok Kim, Taejon (KR); Sung-Ho Park, Taejon (KR)

(73) Assignee: SK Corporation, Seoul (KR)

( * ) Notice: Subject to any disclaimer, the term of this patent is extended or adjusted under 35 U.S.C. 154(b) by 311 days.

(21) Appl. No.: 10/332,171

(22) PCT Filed: Jul. 12, 2001

(86) PCT No.: PCT/KR01/01202

§ 371 (c)(1),
(2), (4) Date: Jan. 3, 2003

(87) PCT Pub. No.: WO02/04431

PCT Pub. Date: Jan. 17, 2002

(65) Prior Publication Data

US 2004/0092738 A1 May 13, 2004

(30) Foreign Application Priority Data

Jul. 12, 2000 (KR) ................................. 2000-0039815
Jun. 9, 2001 (KR) ................................. 2001-0032365

(51) Int. Cl.
*C12Q 1/44* (2006.01)

(52) U.S. Cl. ........................................ 435/19; 435/968
(58) Field of Classification Search ............... 435/19, 435/968; 44/349; 208/17; 252/301.16; 549/283; 585/5; 436/29, 56, 172
See application file for complete search history.

(56) References Cited

U.S. PATENT DOCUMENTS

| | | | |
|---|---|---|---|
| 5,498,808 A | 3/1996 | Smith | |
| 5,672,182 A | 9/1997 | Smith | |
| 5,958,780 A * | 9/1999 | Asher et al. | .................. 436/56 |
| 5,980,593 A | 11/1999 | Friswell et al. | |
| 5,984,983 A * | 11/1999 | Asgaonkar et al. | ........... 44/385 |
| 6,274,381 B1 * | 8/2001 | Pauls et al. | .................. 436/56 |

* cited by examiner

Primary Examiner—Ralph Gitomer
(74) Attorney, Agent, or Firm—Alston & Bird LLP

(57) ABSTRACT

A silent marker, method of marking a petroleum product with the silent marker, and method of detecting the silent marker. The marker is an ester derivative of fluorescent material, and the silent marker may be detected by measuring the fluorescence generated from the selective hydrolysis of the ester moiety under enzymatic action.

21 Claims, 3 Drawing Sheets

SILENT MARKER FOR AN OIL PRODUCT AND ASSOCIATED DETECTION METHOD

This application is filed in accordance with 35 U.S.C. 371 as a National Stage Application of PCT/KR01/01202, filed Jul. 12, 2001, which claims priority to Applications KR 2000/0039815, filed Jul. 12, 2000, and KR 2001/0032365, filed Jun. 9, 2001.

TECHNICAL FIELD

The present invention relates to marking a petroleum product with a silent marker and to the detection of the silent marker. More particularly, the present invention is directed to a method for marking a petroleum product with a silent marker which is ester derivative of fluorescent material and a method for detecting the silent marker by measuring the fluorescence generated therefrom by use of enzymatic hydrolysis.

PRIOR ART

Recently, the sale of counterfeit petroleum products has been dramatically increased for a variety of reasons, for example, government tax policies, the rising price of raw materials for petroleum products, and the like. Further, when considering the serious effects of counterfeit fuels on the life span of vehicles and the environment, it is required to prevent the use thereof. However, since it is very difficult to identify such counterfeit petroleum products with the naked eye, complicated chemical analyses should be carried out.

The term "fluorescent material" as used herein is defined as a substance which, when irradiated with light of specific wavelength, generates light with a different wavelength from that of the applied light by forming an electronic resonance structure. As such, even though a fluorescent material is present at a small amount in petroleum products, it may be detected with ease by irradiating visible light or ultraviolet thereto. However, most fluorescent materials have poor solubility in the petroleum products such as gasoline.

Herein, "marker" means a substance in which a $C_4$–$C_{18}$ hydrocarbon group is attached to a reactive site of the fluorescent material through esterification. The marker as mentioned above show high solubility in the petroleum products, and do not exhibit fluorescence themselves since they have lost the electronic resonance structure owing to esterification. However, when the ester moiety is decomposed therefrom, the fluorescent material is so soluble in water as to re-exhibit fluorescence. Thus, if petroleum products are marked with such a marker prior to distribution, it can be confirmed whether or not the genuine petroleum products are replaced and/or blended with low priced products manufactured by another company, or low-grade products, by quantitatively analyzing the fluorescence of the marker in the petroleum products on distribution network. Further, the lightly taxed products may be identified from the similar products subject to higher taxes in the same way as explained above.

In this regard, U.S. Pat. No. 5,980,593 discloses linear or branched $C_1$–$C_{18}$ alkyl acid ester 7-hydroxy-4-methylcoumarin as a silent fluorescent material for marking petroleum products. In the conventional techniques, including the above patent, chemical methods have been employed for the identification of the silent marker, in which the ester moiety is decomposed using alkaline solution. However, the fluorescent material may be destroyed during the above procedure, which makes it very difficult to analyzing the fluorescent material quantitatively. Thus, the fluorescent materials available for the conventional methods are considerably limited. Furthermore, other fluorescent materials, which are present naturally in petroleum products, can be extracted by alkaline solution along with the desired fluorescent materials, thereby preventing accurate quantitative analysis of the silent marker.

In particular, additional heating equipments and catalysts are required to carry out the above-mentioned procedures. Thus, it not only takes a long time to detect fluorescence, but also it lacks practical effectiveness. Also, the ester moiety is relatively stable, so that other moieties which are less stable than ester moiety are decomposed by the alkaline solution. As a result, the silent marker employable in the conventional methods is limited to the specific ones, for instance marker as disclosed in the above patent.

DESCLOSURE OF THE INVENTION

It is an object of the present invention to provide a silent marker, which is ester derivative of fluorescent material, suitable for marking a petroleum product.

It is another object of the present invention to provide a composition for detecting a silent marker, which includes an enzyme or a polymer-linked enzyme capable of selectively hydrolyzing the ester moiety of the silent marker.

It is a further object of the present invention to provide a silent marking method for a petroleum product.

It is a further object of the present invention to provide a detection method of a silent marker for a petroleum product using an enzyme or a polymer-linked enzyme capable of selectively hydrolyzing the ester moiety of the silent marker.

It is still another object of the present invention to provide a method for identifying a petroleum product through enzymatic action.

In accordance with first aspect of the present invention, there are provided silent markers represented by the following Formulas I, II and III:

Formula I

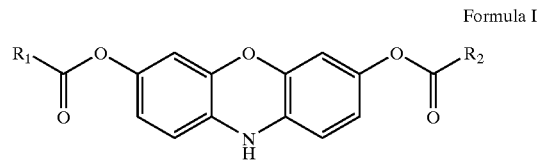

wherein, $R_1$ and $R_2$, which are the same or different, are a $C_4$–$C_{18}$ alkyl group.

Formula II

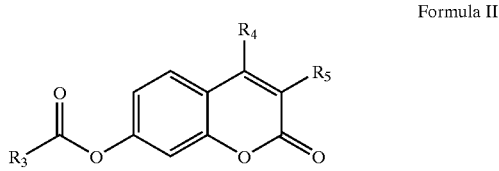

wherein, $R_3$ is a $C_4$–$C_{18}$ alkyl group; $R_4$ is a hydrogen atom, methyl group or trifluoromethyl group; and $R_5$ is a hydrogen atom, a halogen atom or cyano group.

Formula III

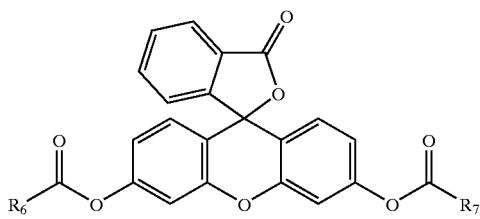

wherein, $R_6$ and $R_7$, which are the same or different, are a $C_{19}$–$C_{24}$ alkyl group.

In accordance with the second aspect of the present invention, there is provided a silent marking method for a petroleum product, in which a marker is added to the petroleum product, said marker being an ester derivative of fluorescent material.

In accordance with the third aspect of the present invention, there is provided a detection method of a silent marker for a petroleum product, comprising the steps of:

a) marking the petroleum product with the silent marker, which is an ester derivative of fluorescent material;

b) adding the petroleum product with an detection composition containing an enzyme capable of specifically decomposing the ester moiety of the silent marker; and c) measuring the fluorescence generated from the step b).

In accordance with the fourth aspect of the present invention, there is provided a method for identifying a petroleum product, comprising the steps of:

a) adding the petroleum product having been marked with a silent marker, which is an ester derivative of fluorescent material, with a composition containing an enzyme capable of specifically decomposing the ester moiety of the marker; and b) measuring the fluorescence generated from the step a).

In accordance with the fifth aspect of the present invention, there is provided a composition for detection of a silent marker, which is an ester derivative of fluorescent material, in a petroleum product, wherein said composition comprises an aqueous solution of pH 7 or higher containing an enzyme capable of selectively hydrolyzing the ester moiety of the marker.

BRIEF DESCRIPTION OF THE DRAWINGS

The above objects, and other features and advantages of the present invention will become more apparent from the following detailed description when taken in conjunction with the drawings, in which.

BEST MODES FOR CARRYING OUT THE INVENTION

Figure 1:
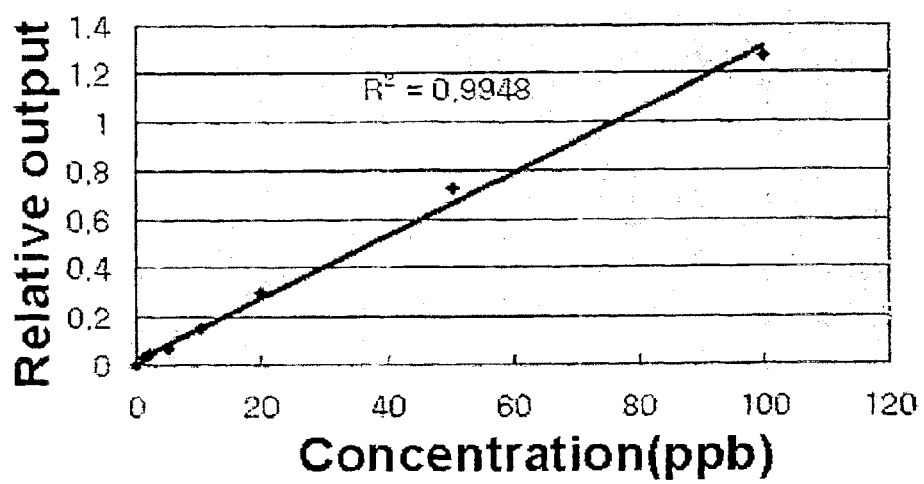
FIG. 1 is a graph illustrating the quantitative analysis of petroleum for resorufin dipalmitate content up to 100 ppb by use of a potable fluorometer according to Example 12 of the present invention.

In accordance with the present invention, the silent marker refer to an ester derivative of fluorescent material, in which a hydrocarbon group is attached to a reactive site such as a hydroxyl group, of the fluorescent material, through esterification. There are no limitations as to the silent marker employable herein, with the proviso that said silent marker is capable of regaining fluorescence through hydrolyzing the ester moiety thereof. In particular, alkyl acid esters of resorufin, fluorescein or coumarin may preferably be used as a silent marker.

The silent markers in accordance with the present invention may be represented by the following Formulas I, II and III;

Formula I

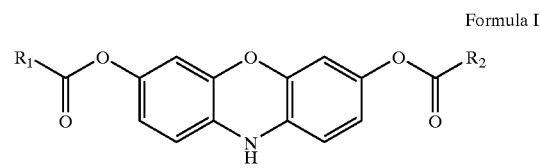

wherein, $R_1$ and $R_2$, which are the same or different, are a $C_4$–$C_{18}$ alkyl group. Preferably, each of $R_1$ and $R_2$ is a $C_{15}H_{31}$ group.

Formula II

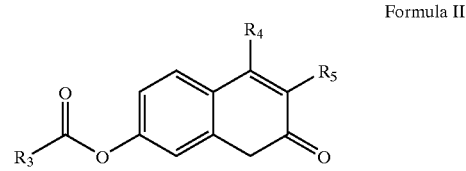

wherein, $R_3$ is a $C_4$–$C_{18}$ alkyl group; $R_4$ is a hydrogen atom, methyl group or trifluoromethyl group; and $R_5$ is a hydrogen atom, a halogen atom or cyano group. Preferably, $R_3$ is a $C_{15}H_{31}$ group, $R_4$ is a methyl group, and $R_5$ is a chlorine atom.

Formula III

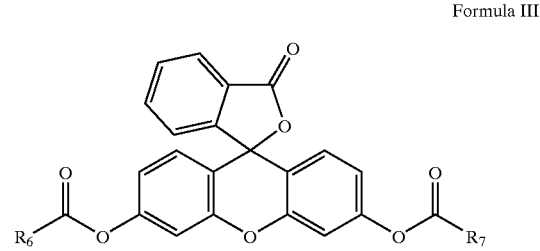

wherein, $R_6$ and $R_7$, which are the same or different, are a $C_{19}$–$C_{24}$ alkyl group. Especially, $R_6$ and $R_7$ serve to increase the solubility of the silent marker of Formula III in organic liquids.

In the present invention, representatives of said silent marker include ester derivatives of 7-hydroxy-4-trifluoromethyl coumarin, 7-hydroxy coumarin, 3-cyano-7-hydroxy-4-methyl coumarin, 4-hydroxy coumarin, 7-hydroxyl-4-methyl coumarin (U.S. Pat. No. 5,980,593), 3-chloro-7-hydroxy-4-methyl coumarin and 3-chloro-7- hydroxy-4-methyl coumarin, ester derivatives of resorufin, ester derivatives of fluorescein (U.S. Pat. No. 5,498,808), and a mixture thereof.

According to the present invention, as the petroleum product to which the above marker is added, there may be used fuel for vehicles such as gasoline, liquefied natural gas (LNG), liquefied petroleum gas (LPG), diesel fuel, kerosene, heavy oil, and the like. Thus, petroleum products for various uses, which are manufactured and/or distributed by tax evaders, as well as counterfeit petroleum products prepared by mixing organic solvents such as benzene, toluene and the like, can be identified with ease.

In the present invention, the marker may be used at an amount of 0.01–30 ppm, preferably, 0.5–10 ppm in the petroleum product. When detected, the fluorescent material corresponding to the silent marker releases a unique fluorescence wavelength from one another. In the case where the petroleum product is marked using a mixture of two kinds of markers, which are mixed with each other at known ratio, the third fluorescence resulting from the combination of two different fluorescences may be detected. In this regard, for example, it is possible to mark gasoline and kerosene with different silent markers.

Furthermore, since the silent marker is added to the petroleum product at the predetermined amount, it can be detected so quantitatively that an amount of the marked petroleum product in the sample can be determined. That is, if the marker is added to the genuine petroleum product at a constant amount, it is possible to confirm not only whether or not the petroleum product is genuine by observing the developed fluorescence, but also whether the petroleum product is blended with other liquids by measuring the intensity of the fluorescence.

According to the present invention, in order to detect the marker, there is used an enzyme capable of selectively hydrolyzing the ester moiety of the marker. In particular, an aqueous solution (pH 7 or higher) containing a constant concentration of enzyme is dispensed into a detection kit at a constant amount and then lyophilized to increase the accessibility to organic liquids and the reproductivity of the reaction for detection. There is disclosed the above method for improving the reproductivity of the reaction using a lyophilized enzyme in Korean Patent No. 162270.

Preferably, an enzyme suitable for the present invention is selected from the group consisting of lipase, esterase and cellulase, which may be obtained from various microorganisms or from the internal organs of animals. Most of these enzymes work at a relatively high temperature, for example 50° C. or higher, and have such excellent heat stability that the composition for detecting the marker can be stored with ease. Among them, lipase is more stable in organic liquids than other enzymes, since it acts in vivo as a digestive enzyme for fat.

Further, the enzyme may be used with a (or one or more) polymeric moiety (hydrocarbon polymeric moiety) linked thereto in order to increase both solubility and stability of the enzyme in organic liquids. Preferably, this hydrocarbon polymer(s) to be linked to the enzyme has a molecular weight of 2000 Daltons or higher, and polyethyleneglycol (PEG), Triton X and the like can be preferably used with more preference.

For linking the enzyme to the polymeric moiety, a compound containing both a portion capable of reacting with amine groups, sulfhydryl groups, or hydroxyl groups in amino acids; and a portion capable of reacting with hydroxyl groups in the polymer, can be preferably used as a linker. The exemplified structure in which the enzyme is linked to polymeric moieties by the linker such as cyanuric chloride, is represented by the following Formula IV:

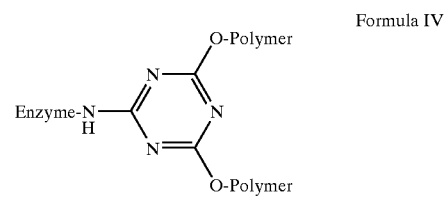

Formula IV

In the linking reaction between the enzyme and the polymer, a lysine residue, which exists on the surface of the enzyme, may be linked to the polymer at a ratio of either 1:1 or 2:1, since the mixing ratio between the enzyme and the polymer varies with the number of lysine residues on the enzyme.

In the case where the enzyme linked to the polymeric moiety is used for the detection of the marker, there are provided the following advantages.

Firstly, proteases, which may deactivate the enzyme, can be prevented from accessing the enzyme. Secondly, the environment in which the enzyme forms an active three-dimensional structure through hydrogen bonds with water molecules is also established within organic solvents such that the enzyme activity can be greatly improved therein. Thirdly, enzyme activity is conserved for over 3 months even though the enzyme is stored in organic solvent at room temperature, since the destruction of the three dimensional structure of the enzyme, which is caused by exposure of the hydrophobic portion of enzyme to the solvent as the temperature increases (Inada, Y. et al., 1986), is prevented by the hydrocarbon polymeric moiety.

Aqueous solution (pH 7 or higher), which contains the enzyme linked to polymeric moiety described above, can be used as the composition of detection. Preferably, the above aqueous solution is used after lypophilization.

The above aqueous solution is added to the petroleum product marked with a silent marker at a proper ratio and mixed well. Then, the resultant aqueous solution layer is irradiated with light of one specific wavelength, so that light of another specific wavelength is released therefrom. In this case, most lights which are fluoresced from the aqueous solution layer are visible light. For instance, resorufin releases a red light, fluorescein releases a green light, and coumarin releases a blue light. The fluorescence ability results from hydrolysis of ester bond of the silent marker by use of the ester-decomposable enzyme. The enzyme reaction occurs in the phase boundary between petroleum and water, since enzyme in aqueous solution uses water to decompose the ester bond of the marker dissolved in the petroleum phase, and then fluorescent material, which is dissociated from the hydrocarbon moiety of the marker, is released into the water phase. Thus, the fluorescence generated from the water phase can be detected by use of spectrophotofluorometer. Also, where any portable spectrophotofluorometer is used, fluorescence in the petroleum product can be detected easily with precision.

Hereinafter, the present invention will be described in detail with reference to the following examples. The examples are given for illustration of the present invention and are not to be construed as limiting the present invention.

EXAMPLE 1

Synthesis of Resorufin Dipalmitate 1.6 g of resorufin was dissolved in 40 ml of tetrahydrofuran in a 250 ml flask, and then 3.1 g of potassium carbonate and 3.1 ml of triethylamine were added to the solution. After 30 minutes, 7.0 ml of palmitoyl chloride was added thereto and the mixture was stirred for 2 hours at room temperature. Thereafter, 50 ml of distilled water and 250 ml of ethyl acetate were added to extract the title compound into the ethyl acetate phase. The ethyl acetate phase was washed with 200 ml of salt water, and then dried with manganese anhydride. Following the distillation and evaporation of the solvent, the residue was recrystalized with hexane and ethyl acetate to obtain reddish resorufin dipalmitate.

EXAMPLE 2

Synthesis of Fluorescein Dipalmitate 2.5 g of fluorescein was dissolved in tetrahydrofuran in a 250 ml flask, and then 3.1 g of potassium carbonate and 3.1 ml of triethylamine were added to the solution. After 30 minutes, 7.0 ml of palmitoyl chloride was added thereto and the mixture was stirred for 2 hours at room temperature. Next, 50 ml of distilled water and 250 ml of ethyl acetate were added to extract the title compound into the ethyl acetate phase. The ethyl acetate phase was washed with 200 ml of salt water, and then dried with manganese anhydride. Following the distillation and evaporation of the solvent, the residue was recrystalized with hexane and ethyl acetate to obtain fluorescein dipalmitate of the color of skin.

EXAMPLE 3

Synthesis of 3-chloro-4-methyl-7-hydroxy Coumarin Palmitate 2.5 g of 3-chloro-4-methyl-7-hydroxy coumarin was dissolved in 60 ml of tetrahydrofuran in a 250 ml flask, and then 3.6 g of potassium carbonate and 3.6 ml of triethylamine were added to the solution. After 30 minutes, 10.0 ml of palmitoyl chloride was added thereto and the mixture was stirred for 2 hours at room temperature. Thereafter, 50 ml of distilled water and 250 ml of ethyl acetate were added to extract the title compound into the ethyl acetate phase. The ethyl acetate phase was washed with 200 ml of salt water, and then dried with manganese anhydride. Following the distillation and evaporation of the solvent, the residue was recrystalized with hexane and ethyl acetate to obtain white 3-chloro-4-methyl-7-hydroxy coumarin palmitate.

EXAMPLE 4

Synthesis of 7-hydroxy Coumarin Palmitate 1.0 g of 7-hydroxy coumarin was dissolved in 100 ml of pyridine in a 500 ml flask and 2.9 ml of palmitoyl chloride was added to the solution, followed by stirring at room temperature. After reaction for 3 hours, pyridine was removed by evaporation under vacuum. Addition of distilled water and methylene chloride at ratio of 1:1 allowed the title compound to be extracted into the methylene chloride phase. The methylene chloride phase was subjected to chromatography eluting with methylene chloride only. The solvent was removed from the first eluate to obtain white 7-hydroxy coumarin palmitate.

EXAMPLE 5

Synthesis of 3-chloro-4-methyl-7-hydroxy Coumarin Laurate 2.5 g of 3-chloro-4-methyl-7-hydroxy coumarin was dissolved in 60 ml of tetrahydrofuran in a 250 ml flask, followed by the addition of 3.6 g of potassium carbonate and 3.6 ml of triethylamine. After 30 minutes, 8.0 ml of lauroyl chloride was added thereto and the mixture was stirred for 2 hours at room temperature. Thereafter, 50 ml of distilled water and 250 ml of ethyl acetate were added to extract the title compound into the ethyl acetate phase. The ethyl acetate phase was washed with 200 ml of salt water, and then dried with anhydrous manganese. Following the distillation and evaporation of the solvent, the residue was recrystalized with hexane and ethyl acetate to obtain white 3-chloro-4-methyl-7-hydroxy coumarin laurate.

EXAMPLE 6

Preparation of Reagent Containing Lipase for Detection

At 4° C., 1 g of the lipase purified from *Pseudomonas cepacis* was completely dissolved in 25 ml of a 100 mM Tris buffer adjusted to pH 8.0 with hydrochloric acid. After being dispensed by 20 ul into 2 ml tubes, the solution was dried on Centra evaporator™ (Bioneer Corporation, Korea) and stored frozen.

EXAMPLE 7

Preparation of Lipase Linked to Polyethyleneglycol 20.00 g of monomethoxypolyethyleneglycol (M.W. about 4,500) was dissolved, along with 0.37 g of cyanuric chloride as a linker, in 100 ml of benzene in a 500 ml flask. After the addition of 6.5 g of $NaCO_3$ thereto, the reaction was conducted at 80° C. for 40 hours. Prepared by substituting a methoxy group for one of the two terminal hydroxyl groups of polyethylene glycol, the monomethoxypolyethyleneglycol is a hydrocarbon polymer containing only one active hydroxyl group. Salts were filtered off and the solvent was removed to give white solids. 5 g of the solids were dissolved, along with 78 mg of a lipase purified from *Pseudomonas cepacis*, in 25 ml of a 100 mM Tris buffer adjusted to pH 8.0 with hydrochloric acid, and the reaction was carried out for 2 hours at 4° C. After the removal of unreacted polyethylene glycol by filtration with a 1 kDa cutoff, the solution was dispensed into 1.5 ml tubes by 20 $\mu$L, dried on a Centra evaporator™ (Bioneer Corporation, Korea) and stored frozen. This was used as a detecting composition in subsequent experiments.

EXAMPLE 8

Qualitative Detection of Resorufin Dipalmitate in Petroleum

To the enzyme solution for detection obtained in Example 6 were added 0.5 ml of distilled water and 1.0 ml of petroleum containing 1 ppm of the resorufin dipalmitate obtained in Example 1, followed by stirring the solution. When the aqueous phase was irradiated with natural light, red light was detected by the naked eye.

EXAMPLE 9

Qualitative Detection of Fluorescein Dipalmitate in Petroleum

To the enzyme solution for detection obtained in Example 6 were added 0.5 ml of distilled water and 1.0 ml of petroleum containing 1 ppm of fluorescein dipalmitate obtained in Example 2, followed by stirring the solution. When the aqueous phase was irradiated with natural light, green light was detected by the naked eye.

EXAMPLE 10

Qualitative Detection of 3-chloro-4-methyl-7-hydroxycoumarin Palmitate in Petroleum To the enzyme solution for detection obtained in Example 6 were added 0.5 ml of distilled water and 1.0 ml of petroleum containing 10 ppm of 3-chloro-4-methyl-7-hydroxycoumarin palmitate obtained in Example 3, followed by stirring the solution. When the aqueous phase was irradiated with light of wavelength of 365 nm, blue light was detected by the naked eye.

EXAMPLE 11

Qualitative Detection of a Mixture of Resorufin Dipalmitate and 3-chloro-4-methyl-7-hydroxycoumarin Palmitate in Petroleum Resorufin dipalmitate and 3-chloro-4-methyl-7-hydroxycoumarin palmitate obtained in Examples 1 and 3 were added to petroleum in amounts of 1 and 10 ppm, respectively. To the enzyme solution obtained in Example 6 were added 0.5 ml of distilled water and 1.0 ml of petroleum containing the markers, followed by stirring the solution. When the aqueous phase was irradiated by light of wavelength of 365 nm, violet light was detected by the naked eye.

EXAMPLE 12

Quantitative Detection of Resorufin Dipalmitate in Petroleum

Kerosene containing 100 ppb (w/v) of the marker obtained in, Example 1 was diluted by 0/100, 1/100, 2/100, 10/100, 20/100 and 100/100 to give solutions of 0 ppb, 1 ppb, 2 ppb, 5 ppb, 10 ppb, 20 ppb, 50 ppb and 100 ppb respectively, each of which was then dispensed by 1 ml to the enzyme solution obtained in Example 6, followed by mixing with 1.5 ml of distilled water. While the aqueous phase was irradiated with light of wavelength of 570 nm, the fluorescent light at 585 nm was quantitatively measured by use of a fluorometer, and the result is depicted in FIG. 1.

EXAMPLE 13

Quantitative Detection of Fluorescein Dipalmitate in Petroleum

Figure 2:
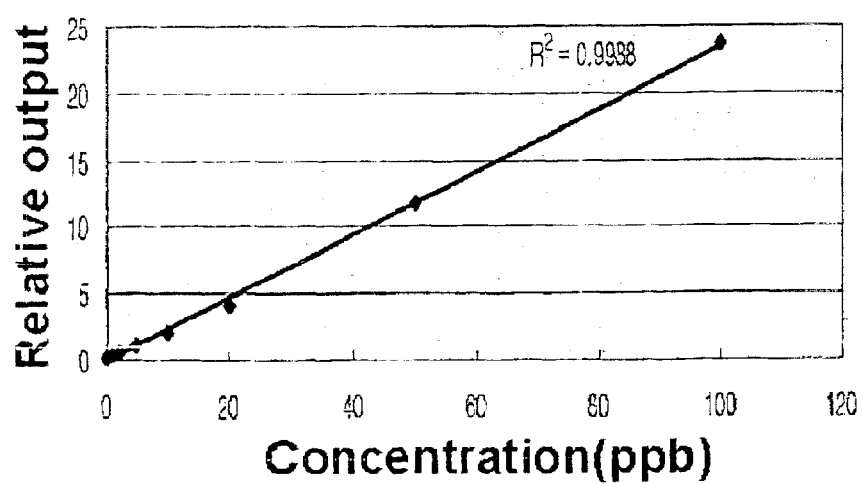
FIG. 2 is a graph illustrating the quantitative analysis of petroleum for fluoresceine dipalmitate content up to 100 ppb by use of a potable fluorometer according to Example 13 of the present invention.

Petroleum containing 100 ppb(w/v) of the marker obtained in Example 2 was diluted by 0/100, 1/100, 2/100, 5/100, 10/100, 20/100, 50/100 and 100/100 to give solutions of 0 ppb, 1 ppb; 2 ppb; 5 ppb; 10 ppb; 20 ppb, 50 ppb and 100 ppb, respectively, each of which was dispensed by 1 ml into the enzyme solution obtained in Example 6, followed by mixing with 1.5 ml of distilled water. The aqueous phase was irradiated with light of wavelength of 490 nm, the fluorescent light at 514 nm was quantitatively measured by use of a fluorometer, and the result is illustrated in FIG. 2.

EXAMPLE 14

Figure 3:
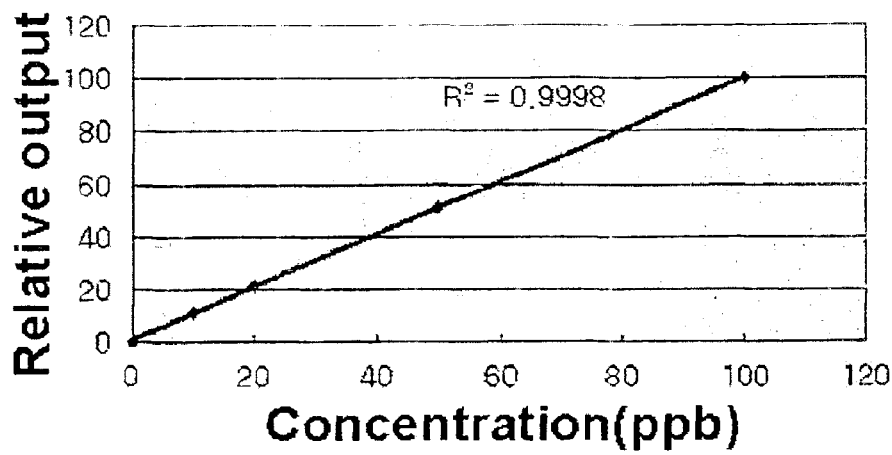
FIG. 3 is a graph illustrating the quantitative analysis of petroleum for 3-choro-4-methyl-7-hydroxy coumarin palmitate content up to 100 ppb by use of a potable fluorometer according to Example 14 of the present invention.

Quantitative Detection of 3-chloro-4-methyl-7-hydroxycoumarin Palmitate in Petroleum Petroleum containing 100 ppb(w/v) of the marker obtained in Example 3 was diluted by 0/10, 1/10, 2/10, 5/10 and 10/10 to give solutions of 0 ppb, 10 ppb, 20 ppb, 50 ppb, 100 ppb, respectively, each of which was dispensed by 1 ml into the enzyme solution obtained in Example 6, followed by the mixing 1.5 ml of distilled water. The aqueous phase was irradiated with light of wavelength of 350 nm, the fluorescent light at 470 nm was quantitatively measured by use of a fluorometer, and the result is illustrated in FIG. 3.

EXAMPLE 15

Quantitative Detection of 4-methyl-7-hydroxycoumarin Palmitate in Petroleum

Petroleum containing 100 ppb(w/v) of 4-methyl-7-hydroxycoumarin palmitate was diluted by 0/10, 1/10, 2/10, 5/10 and 10/10 to give solutions of 0 ppb, 10 ppb, 20 ppb, 50 ppb, and 100 ppb, respectively, each of which was dispensed by 1 ml into the enzyme solution obtained in Example 6, followed by mixing with 1.5 ml of distilled water. While aqueous phase was irradiated with light of wavelength of 365 nm, the fluorescent light at 470 nm was quantitatively measured by use of a fluorometer.

EXAMPLE 16

Qualitative Detection of Fluorescein Dipalmitate in Petroleum

To the enzyme solution obtained in Example 7, distilled water and petroleum containing 10 ppm of fluorescein palmitate obtained in Example 2 were added in the same amount, followed by stirring. When the aqueous phase was irradiated with ultraviolet light of wavelength of 365 nm, blue light was detected by the naked eye.

EXAMPLE 17

Qualitative Detection of 3-chloro-4-methyl-7-hydroxycoumarin Palmitate in Petroleum To the enzyme solution obtained in Example 7, distilled water and petroleum containing 10 ppm of 3-chloro-4-methyl-7-hydroxycoumarin palmitate of Example 3 were added in the same amount, followed by stirring. When the aqueous phase was irradiated with ultraviolet light of wavelength of 365 nm, the blue light was detected by the naked eye.

EXAMPLE 18

Qualitative Detection for Petroleum Containing a Mixture of Fluorescein Dipalmitate and 3-chloro-4-methyl-7-hydroxycoumarin Palmitate In petroleum were dissolved fluorescein dipalmitate and 3-chloro-4-methyl-7-hydroxycoumarin palmitate, which were obtained in Example 2 and 3, respectively. To the enzyme solution obtained, in Example 7, distilled water and the petroleum containing the markers as above were added in the same amount, followed by stirring. When the aqueous phase was irradiated with ultraviolet light of wavelength of 365 nm, yellowish light was detected by the naked eye.

EXAMPLE 19

Quantitative Detection of Fluorescein Dipalmitate in Petroleum

Figure 5:
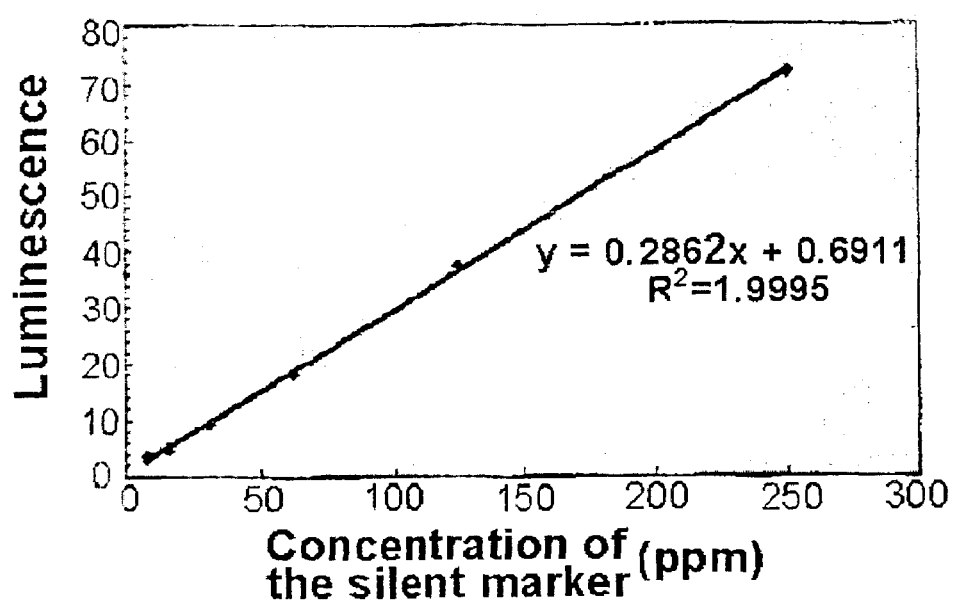
FIG. 5 is a graph illustrating the relationship between the luminescence and the concentration of the silent marker according to Example 19 of the present invention.

Petroleum containing 250 ppm(w/v) of fluorescein palmitate obtained in Example 2 was diluted by 1, 1/2, 1/4, 1/8, 1/16 and 1/32 to give solutions of 250 ppm, 125 ppm, 62.5 ppm, 31.3 ppm, 15.6 ppm and 7.8 ppm respectively, each of which was dispensed by 0.5 ml into the enzyme solution obtained in Example 7, followed by mixing with 0.6 ml of distilled water. After 0.5 ml of the aqueous phase was diluted by 4 folds, fluorescent light emitted from the diluted aqueous phase was quantitatively measured by use of a spectrofluorometer (JASCO. FP-750). The results are depicted in FIG. 5 in which the intensity of fluorescent light at 450 nm is linearly plotted versus the concentration of the labeling material.

EXAMPLE 20

Quantitative Detection of 3-chloro-4-methyl-7-hydroxycoumarin Palmitate

Figure 4:
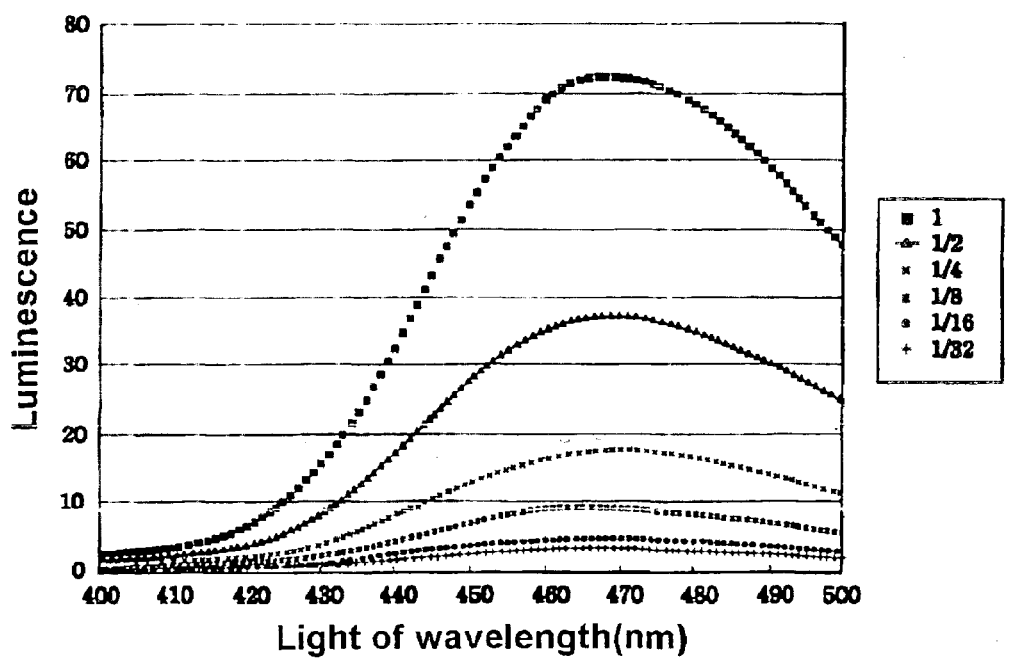
FIG. 4 is a graph illustrating the quantitative analysis of petroleum for a fluorescent material excited with light of wavelength of 350 nm by use of a spectrofluorometer according to Example 20 of the present invention.

Petroleum containing 250 ppb(w/v) of 3-chloro-4-methyl-7-hydroxycoumarin palmitate obtained in Example 3 was diluted by 1, 1/2, 1/4, 1/8, 1/16 and 1/32 to give solutions of 250 ppm, 125 ppm, 62.5 ppm, 31.3 ppm, 15.6 ppm and 7.8 ppm, respectively, each of which was dispensed by 0.5 ml into the enzyme solution obtained in Example 7, followed by mixing with 0.6 ml of distilled water. After the dilution of the aqueous phase by 4 folds, fluorescent light emitted from the diluted aqueous phase was quantitatively measured by use of a spectrofluorometer (JASCO. FP-750). When irradiated with light of wavelength of 350 nm, a maximal peak was obtained at 470 nm, as shown in FIG. 4.

INDUSTRIAL APPLICABILITY

The present invention has very high sensitivity since enzyme, which can selectively hydrolyze ester moiety, is used to detect the silent marker and background signal by fluorescent material present naturally in the petroleum product can be greatly reduced. Also, the procedures for detecting the marker are very simple and easy since only enzyme solution, which can selectively hydrolyze ester bond, is added to the petroleum product. In addition, the enzyme system of the present invention is capable of detecting several markers in petroleum at the same time.

Where the present invention is applied to genuine petroleum, fluorescence is released only from the genuine petroleum, thus, a counterfeit petroleum can be distinguished from the genuine one. Further, according to the present invention, there is not required a complicated procedure such as chemical analysis for the detection of the marker, whereby the present invention may be carried out by a consumer on the spot. For example, after petroleum containing a marker and water are added to the kit containing the dried enzyme solution and shaken, it can be confirmed whether the petroleum is genuine or not.

What is claimed is:

1. A method for detection of a silent marker in a petroleum product, comprising the steps of:
   a) marking the petroleum product with the silent marker, which is an ester derivative of fluorescent material;
   b) adding a detection composition to the marked petroleum product, wherein the detection composition contains an enzyme that specifically decomposes the ester moiety of the silent marker; and
   c) detecting the presence of the silent marker by measuring the fluorescence generated from step b).

2. The detection method according to claim 1, wherein said marker is represented by the following Formula I:

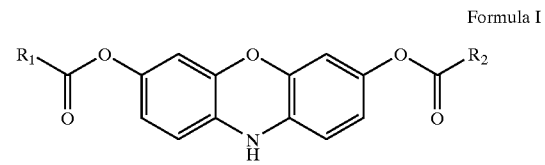

Formula I wherein, $R_1$ and $R_2$, which are the same or different, are $C_4$–$C_{18}$ alkyl group.

3. The detection method according to claim 1, wherein said marker is represented by the following Formula II:

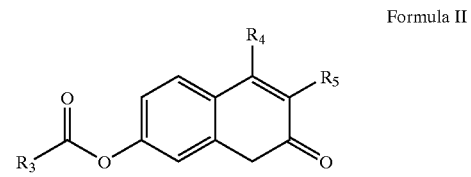

Formula II wherein, $R_3$ is $C_4$–$C_{18}$ alkyl group; $R_4$ is methyl or trifluoromethyl; and $R_5$ is a hydrogen atom, a halogen atom or cyano group.

4. The detection method according to claim 1, wherein said marker is represented by the following Formula III:

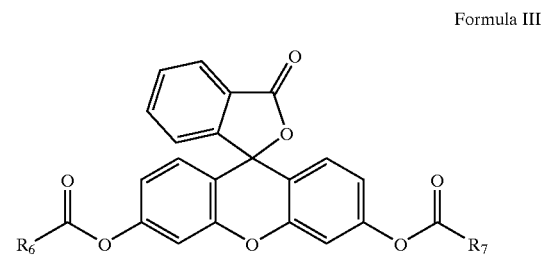

Formula III wherein, $R_6$ and $R_7$, which are the same or different, are a $C_{19}$–$C_{24}$ alkyl group.

5. The detection method according to claim 1, wherein said fluorescent material is selected from the group consisting of ester derivatives of 7-hydroxy-4trifluoromethyl coumarin, 7-hydroxy coumarin,3-cyano-7-hydroxy-4-methyl coumarin, 4-hydroxy coumarin, 7hydroxy-4-methyl coumarin and 3-chloro-7-hydroxy-4methyl coumarin, ester derivatives of resorufin, ester derivatives of fluorescein, and a mixture thereof.

6. The detection method according to claim 3, wherein $R_4$ is methyl and $R_5$ is a chlorine atom.

7. The detection method according to claim 2, wherein each of $R_1$ and $R_2$ is a $C_{15}H_{31}$ group.

8. The detection method according to claim 1, wherein said marker is added in an amount of 0.01–30 ppm to the petroleum product.

9. The detection method according to claim 1, wherein said petroleum product is selected from the group consisting of gasoline, liquefied natural gas (LNG), liquefied petroleum gas(LPG), diesel fuel, kerosene and heavy oil.

10. The detection method according to claim 1, wherein said enzyme selectively hydrolyses the ester moiety of the marker.

11. The detection method according to claim 1, wherein said enzyme is selected from the group consisting of esterase and cellulase.

12. The detection method according to claim 1, wherein said enzyme is lipase.

13. The detection method according to claim 1, wherein said enzyme is linked to at least one polymeric moiety.

14. The detection method according to claim 13, wherein said enzyme is linked to the polymeric moiety by a linker.

15. The detection method according to claim 14, wherein said linker is cyanuric chloride.

16. The detection method according to claim 13, wherein said polymer-linked enzyme is represented by the following general Formula IV;

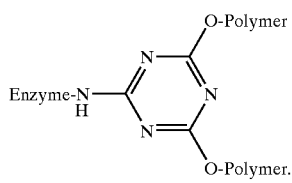

Formula IV

17. The detection method according to claim 13, wherein said polymeric moiety is polyethyleneglycol.

18. A method for identifying a petroleum product, comprising the steps of: a) mixing the petroleum product having been marked with a silent marker, which is an ester derivative of fluorescent material, with a composition containing an enzyme that specifically decomposes the ester moiety of the marker to identify the marked petroleum product; and b) measuring the fluorescence generated from step a).

19. The method according to claim 18, wherein said enzyme selectively hydrolyses the ester moiety of the marker.

20. The method according to claim 18, wherein said enzyme is selected from the group consisting of esterase and cellulase.

21. The method according to claim 18, wherein said enzyme is lipase.

* * * * *